(12) United States Patent
Garofano

(10) Patent No.: US 8,640,270 B1
(45) Date of Patent: Feb. 4, 2014

(54) SPLATTER REDUCTION SYSTEM

(71) Applicant: NUS, LLC, Cedar Grove, NJ (US)

(72) Inventor: Glenn Garofano, Staten Island, NY (US)

(73) Assignee: NUS, LLC, Cedar Grove, NJ (US)

( * ) Notice: Subject to any disclaimer, the term of this patent is extended or adjusted under 35 U.S.C. 154(b) by 0 days.

(21) Appl. No.: 13/782,544

(22) Filed: Mar. 1, 2013

(51) Int. Cl.
*E03D 9/00* (2006.01)
*E03D 1/00* (2006.01)

(52) U.S. Cl.
USPC .......................................................... 4/300.3

(58) Field of Classification Search
USPC .......................................................... 4/300.3
See application file for complete search history.

(56) References Cited

U.S. PATENT DOCUMENTS

| | | | | |
|---|---|---|---|---|
| 3,350,722 A | * | 11/1967 | Moreschini | 4/300.3 |
| 3,590,394 A | * | 7/1971 | Andersson | 4/447 |
| 4,282,611 A | * | 8/1981 | O'Day | 4/144.1 |
| 4,612,676 A | * | 9/1986 | Whitman | 4/300.3 |
| 4,832,046 A | * | 5/1989 | Parrish | 600/584 |
| D414,060 S | * | 9/1999 | Talbot-Titley | D6/516 |
| 6,327,716 B1 | * | 12/2001 | Kaus | 4/144.4 |
| 6,460,200 B1 | * | 10/2002 | Mottale et al. | 4/144.4 |
| D602,156 S | * | 10/2009 | Young | D24/122 |
| D617,895 S | * | 6/2010 | Aguila | D24/122 |
| 2007/0191795 A1 | * | 8/2007 | Di Croce | 604/347 |
| 2010/0024110 A1 | * | 2/2010 | St. John | 4/300.3 |
| 2011/0185485 A1 | * | 8/2011 | Reynolds | 4/246.1 |

* cited by examiner

*Primary Examiner* — Lori Baker

(57) ABSTRACT

A system for reducing splatter on and around a toilet when urinating. The system features a weighted base having a telescopic mounting tube. A posterior base end is placed on a ground surface dose to a toilet. The system features a segmented horizontal arm assembly attached to the mounting tube comprising a first arm segment, a second arm segment, and a third arm segment. The system features a disposable cone storage cone located in the first arm segment containing one or more disposable cones. The system features a brush storage cone located in the second arm segment containing a cleaning solution and a cleaning brush. The system features a urinating cone located in the third arm segment. A urinating aperture is located in a urinating cone posterior end. The system features the toilet having a toilet bowl.

3 Claims, 6 Drawing Sheets

SPLATTER REDUCTION SYSTEM

FIELD OF THE INVENTION

The present invention relates to toilet systems, or more specifically, splatter reducing systems for toilets.

BACKGROUND OF THE INVENTION

Toilets have been in use for many years by both males and females. Because both males and females often use the same toilet, sanitation on and around the toilet becomes very important. The present invention features a system for reducing splatter on and around a toilet when urinating.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a system for reducing splatter on and around a toilet when urinating. In some embodiments, the system comprises a weighted base having a telescopic mounting tube. In some embodiments, a posterior base end is placed on a ground surface close to a toilet. In some embodiments, the system comprises a segmented horizontal arm assembly comprising a first arm segment, a second arm segment, and a third arm segment attached to the mounting tube. In some embodiments, the system comprises a handle located on a terminating third arm segment first end.

In some embodiments, the system comprises a disposable cone storage cone located in the first arm segment. In some embodiments, one or more disposable cones are located in the cone storage cone via stacking. In some embodiments, the system comprises a brush storage cone located in the second arm segment. In some embodiments, a cleaning solution and a cleaning brush are located in the brush storage cone. In some embodiments, the system comprises a urinating cone located in the third arm segment. In some embodiments, a urinating aperture is located in the urinating cone posterior end.

In some embodiments, the system comprises the toilet having a toilet bowl. In some embodiments, the urinating cone is centrally located over the toilet bowl via pivoting the horizontal arm assembly. In some embodiments, a urinating cone height is adjusted via the telescopic mounting tube. In some embodiments, a disposable cone is placed in the urinating cone before urinating, and then discarded into the toilet bowl upon completion of urination. In some embodiments, the brush is used to clean the urinating cone after urination.

DESCRIPTION OF PREFERRED EMBODIMENTS

Figure 1:
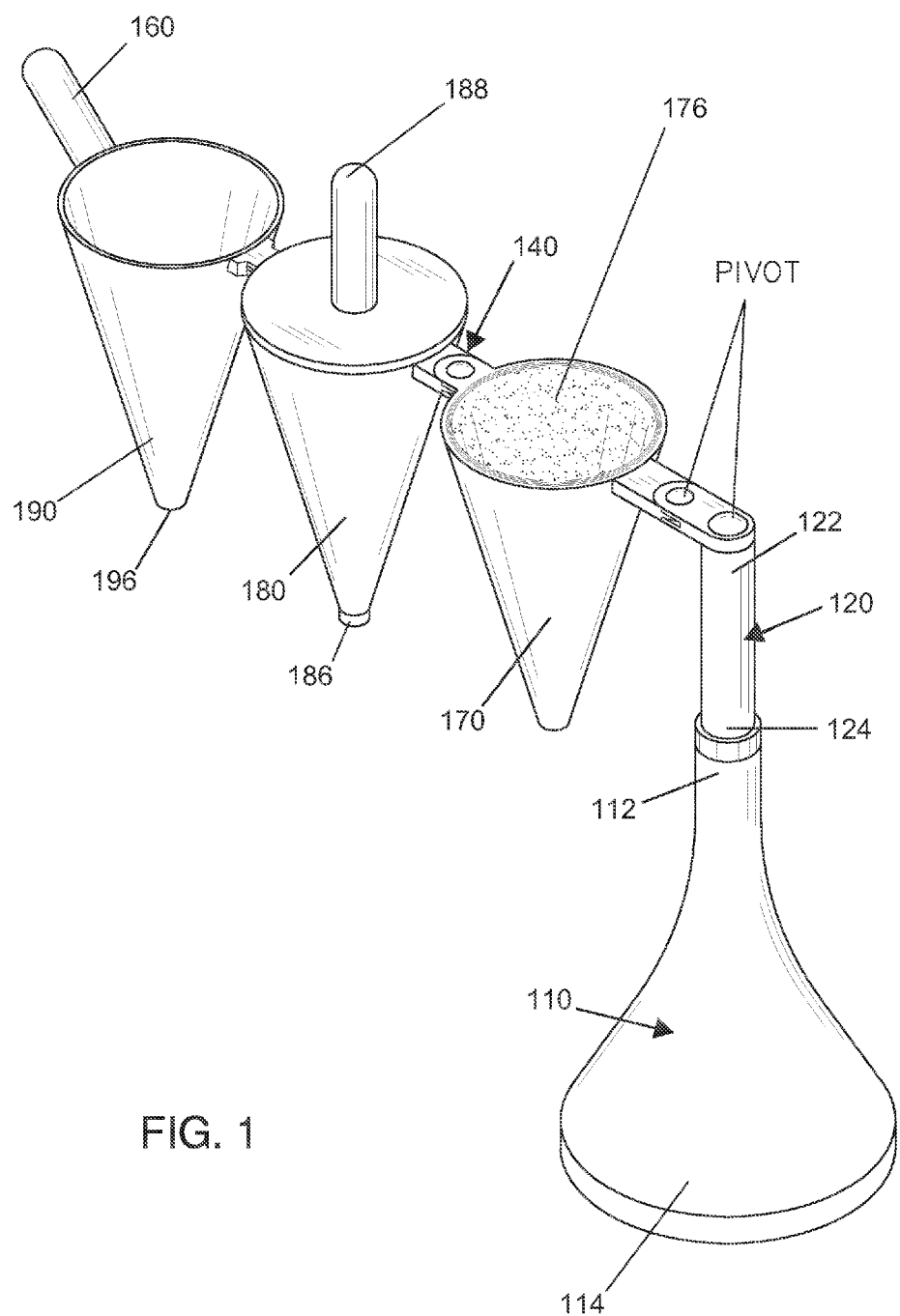
FIG. 1 shows a perspective view of the base, the mounting tube, the horizontal arm assembly, and the cones of the present invention.
Figure 2:
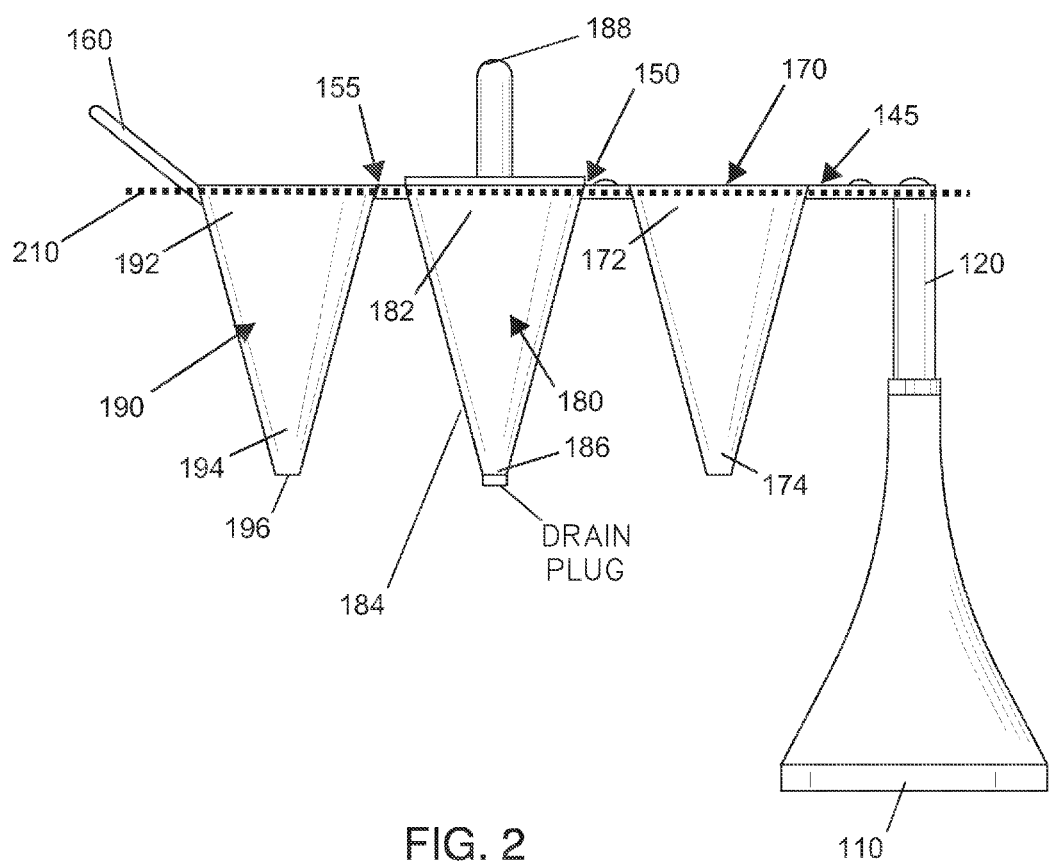
FIG. 2 shows a side view of the base, the mounting tube, the horizontal arm assembly, and the cones of the present invention.
Figure 3:
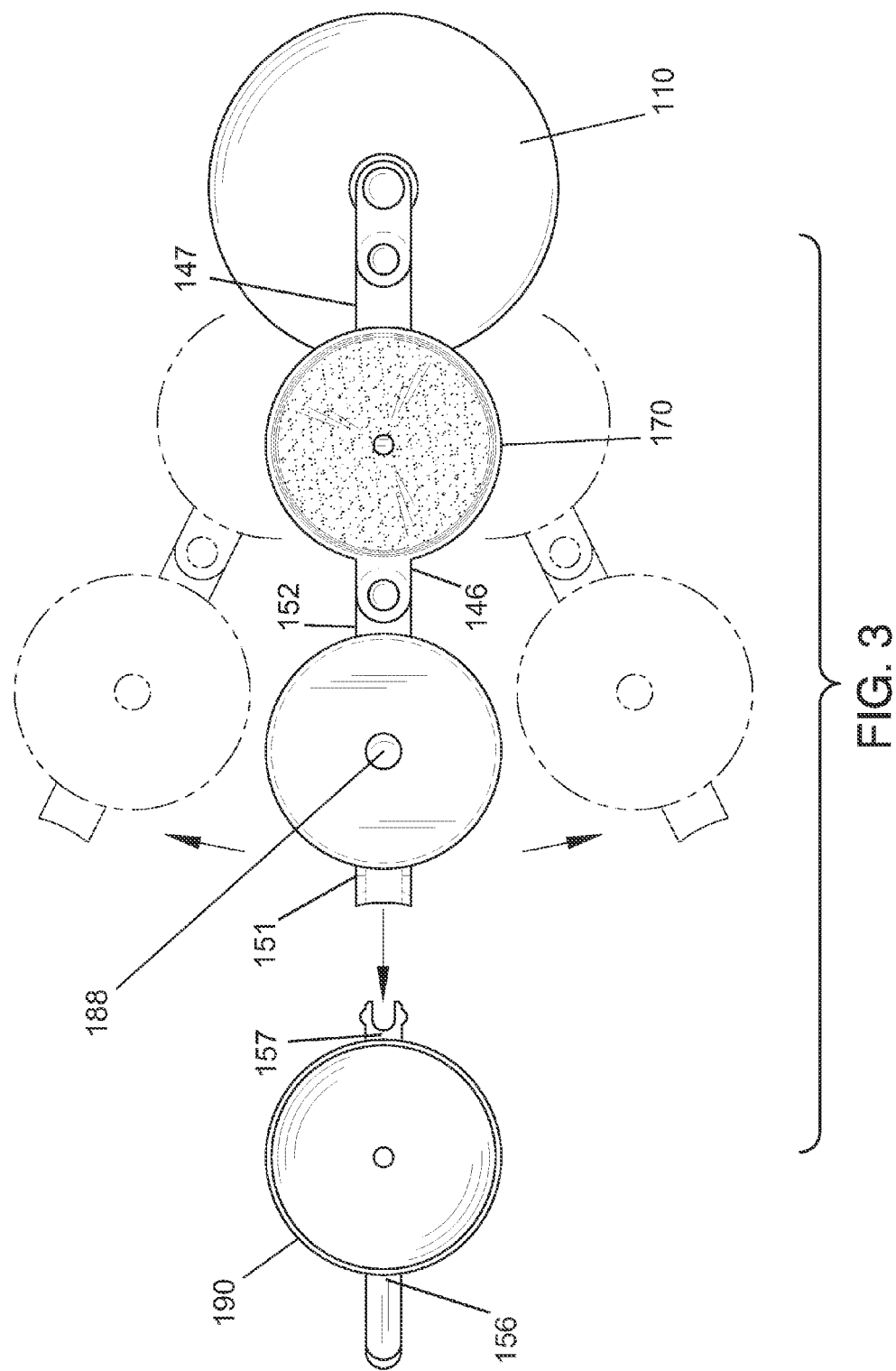
FIG. 3 shows a top view of the base, the mounting tube, the horizontal arm assembly, and the cones of the present invention.
Figure 4:
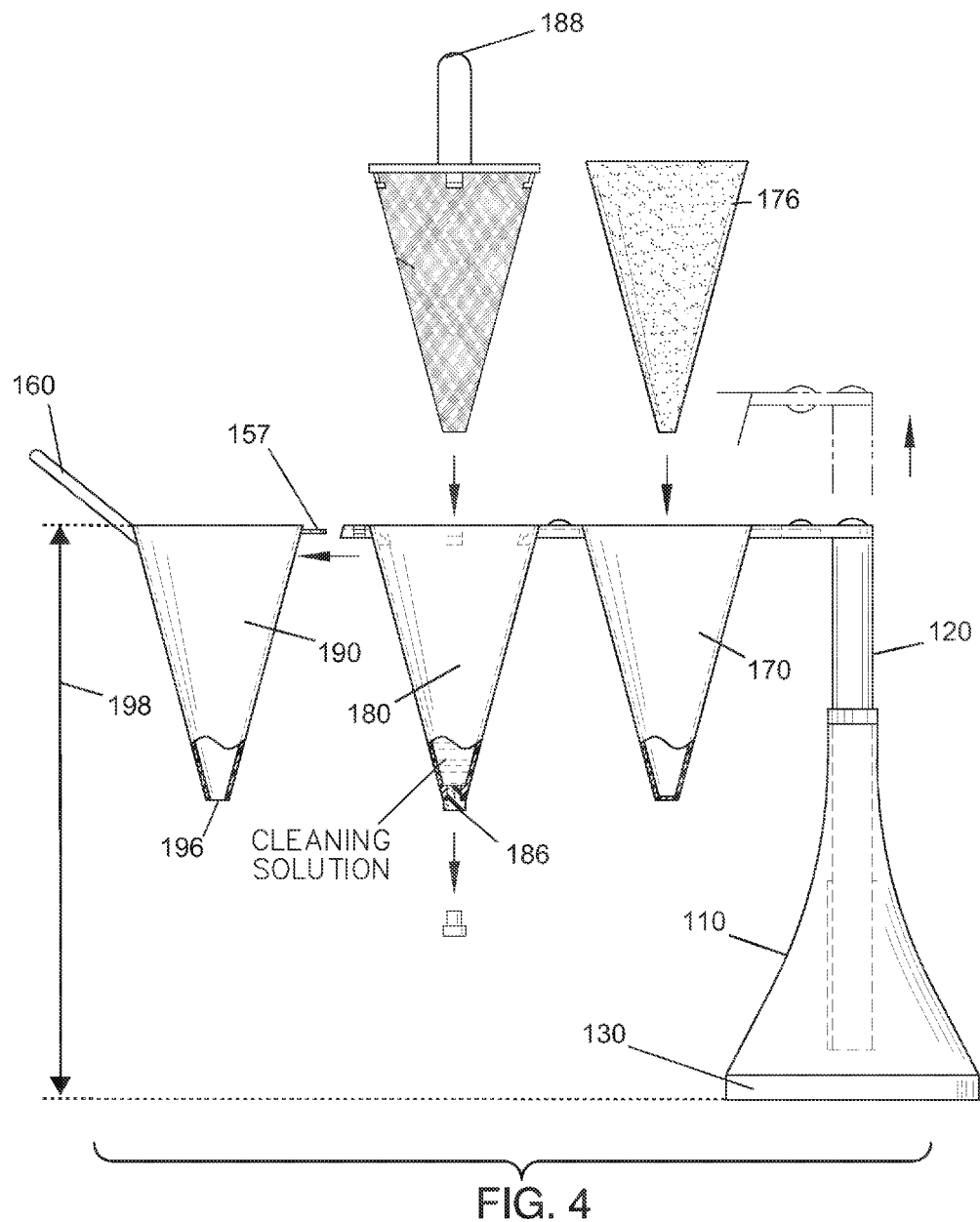
FIG. 4 shows a side view of the base, the mounting tube, the horizontal arm assembly, and the cones of the present invention featuring the cleaning brush and the disposable cone.
Figure 5:
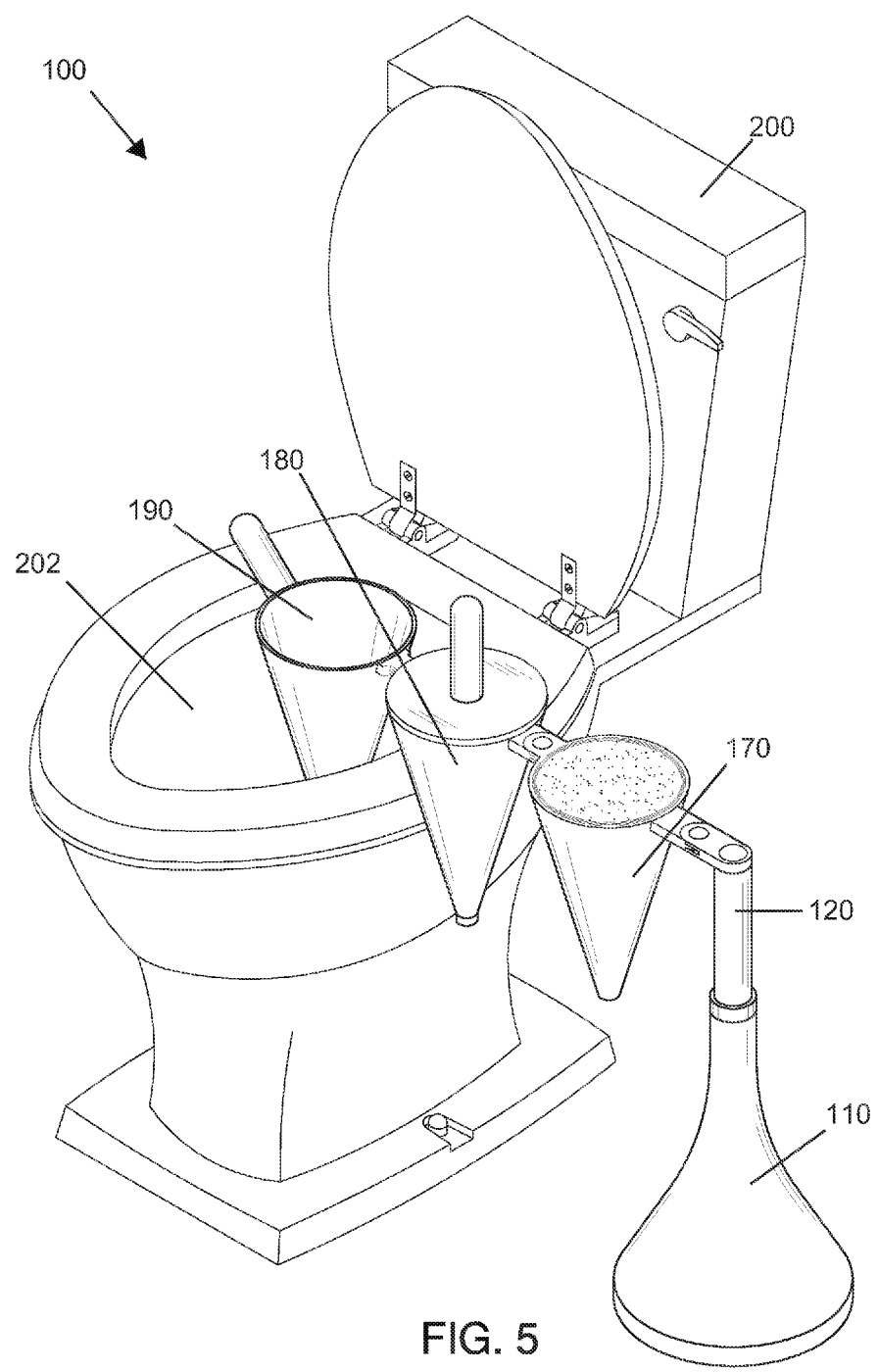
FIG. 5 shows a perspective view of the present invention.

Following is a list of elements corresponding to a particular element referred to herein:
- 100 Urination splatter reduction system
- 110 Base
- 112 Base anterior end
- 114 Base posterior end
- 120 Mounting tube
- 122 Tube anterior end
- 124 Tube posterior end
- 130 Weight component
- 140 Horizontal arm assembly
- 145 First arm segment
- 146 First arm segment first end
- 147 First arm segment second end
- 150 Second arm segment
- 151 Second arm segment first end
- 152 Second arm segment second end
- 155 Third arm segment
- 156 Third arm segment first end
- 157 Third arm segment second end
- 160 Handle
- 170 Cone storage cone
- 172 Cone storage cone anterior end
- 174 Cone storage cone posterior end
- 176 Disposable cone
- 180 Brush storage cone
- 182 Brush storage cone anterior end
- 184 Brush storage cone posterior end
- 186 Drain aperture
- 188 Cleaning brush
- 190 Urinating cone
- 192 Urinating cone anterior end
- 194 Urinating cone posterior end
- 196 Urinating aperture
- 198 Urinating cone height
- 200 Toilet
- 202 Toilet bowl
- 210 Horizontal axis Referring now to FIG. 1-6, the present invention features a splatter reduction system (100) for reducing splatter on and around a toilet (200) when urinating. In some embodiments, the system (100) comprises a weighted base (110) having a base anterior end (112) and a base posterior end (114). In some embodiments, the base anterior end (112) comprises a telescopic mounting tube (120) having a tube anterior end (122) and a tube posterior end (124) located thereon. In some embodiments, the tube posterior end (124) is located on the base anterior end (112). In some embodiments, the tube posterior end (124) projects inside the base (110). In some embodiments, the base posterior end (114) comprises a planar terminating end for placing on a ground surface close to a toilet (200). In some embodiments, the base posterior end (114) comprises a weight component (130) for stability. In some embodiments, the base (110) tapers from the terminating base posterior end (114) to the base anterior end (112).

In some embodiments, the system (100) comprises a segmented horizontal arm assembly (140) comprising a first arm segment (145), a second arm segment (150), and a third arm segment (155). In some embodiments, a first arm segment second end (147) is pivotally located on the tube anterior end (122). In some embodiments, a second arm segment second end (152) is pivotally located on a first arm segment first end (146). In some embodiments, a third arm segment second end (157) is attachably located on a second arm segment first end (151). In some embodiments, the third arm segment second end (157) is attached to the second arm segment first end (151) via a quick disconnect.

Figure 6:
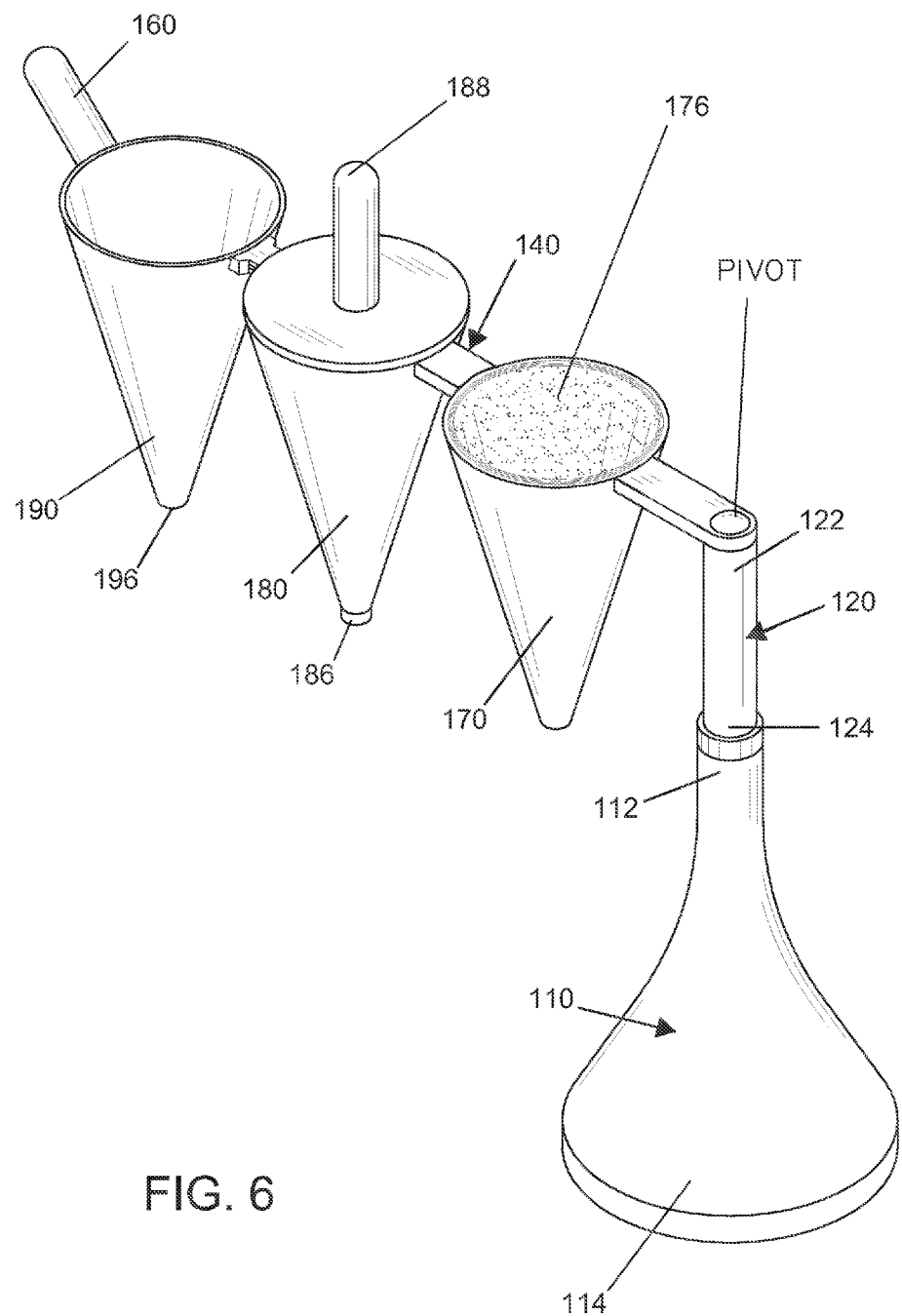
FIG. 6 shows a perspective view of the base, the mounting tube, the horizontal arm assembly, and the cones of an alternate embodiment of the present invention.

In some embodiments, as shown in FIG. 6, the system (100) comprises a horizontal arm assembly (140) comprising a first arm segment (145), a second arm segment (150), and a third arm segment (155). In some embodiment, a first arm segment second end (147) is pivotally located on the tube anterior end (122). In some embodiments, a second arm segment second end (152) is contiguous with a first arm segment first end (146). In some embodiments, a third arm segment second end (157) is attachably located on a second arm segment first end (151).

In some embodiments, the system (100) comprises a handle (160) located on a terminating third arm segment first end (156). In some embodiments, the handle can be used for positioning the horizontal arm assembly (140) and for carrying a urinating cone (190).

In some embodiments, the system (100) comprises a disposable cone storage cone (170) having an open cone storage cone anterior end (172) and a cone storage cone posterior end (174). In some embodiments, the cone storage cone (170) is located in the first arm segment (145) between the first arm segment first end (146) and the first arm segment second end (147). In some embodiments, the cone storage cone (170) tapers from the open cone storage cone anterior end (172) to the cone storage cone posterior end (174). In some embodiments, one or more disposable cones (176) are located in the cone storage cone (170) via stacking. In some embodiments, the disposable cones (176) are biodegradable and able to be discarded in a septic system or sewer system by flushing down the toilet (200). In some embodiments, the disposable cones (176) are paper.

In some embodiments, the system (100) comprises a brush storage cone (180) having an open brush storage cone anterior end (182) and a brush storage cone posterior end (184). In some embodiments, the brush storage cone (180) is located in the second arm segment (150) between the second arm segment first end (151) and the second arm segment second end (152). In some embodiments, the brush storage cone (180) tapers from the brush storage cone anterior end (182) to the brush storage cone posterior end (184). In some embodiments, a drain aperture (186) is located in the brush storage cone posterior end (184). In some embodiments, a cleaning solution is located in the brush storage cone (180). In some embodiments, a cleaning brush (188) is located in the brush storage cone (180) for storage. In some embodiments, the cleaning brush (188) is soaked in the cleaning solution. In some embodiments, the cleaning brush (188) is a tapered, bristled brush. In some embodiments, the drain aperture (186) comprises a plug.

In some embodiments, the system (100) comprises a urinating cone (190) having an open urinating cone anterior end (192) and a urinating cone posterior end (194). In some embodiments, the urinating cone (190) is located in the third arm segment (155) between the third arm segment first end (156) and the third arm segment second end (157). In some embodiments, the urinating cone (190) tapers from the urinating cone anterior end (192) to the urinating cone posterior end (194). In some embodiments, a urinating aperture (196) is located in the urinating cone posterior end (194). In some embodiments, the urinating aperture (196) directs a flow of urine from the urinating cone (190) into a toilet bowl (202).

In some embodiments, the system (100) comprises the toilet (200) having a toilet bowl (202).

In some embodiments, the urinating cone (190) is centrally located over the toilet bowl (202) via pivoting the horizontal arm assembly (140). In some embodiments, a urinating cone height (198) is adjusted via the telescopic mounting tube (120). In some embodiments, a disposable cone (176) is placed in the urinating cone (190) before urinating, and then discarded into the toilet bowl (202) upon completion of urination. In some embodiments, the disposable cone (176) is not used. In some embodiments, the cleaning brush (188) is used to clean the urinating cone (190) after urination.

In some embodiments, the urinating cone (190) comprises an adjustable angle on a horizontal axis (210). In some embodiments, the urinating cone (190) is adjustable via height, angle, and distance from a user.

In some embodiments, the system (100) includes the cone storage cone (170) but no brush storage cone (180) or urinating cone (190). In some embodiments, the system (100) includes the brush storage cone (180) but no cone storage cone (170) or urinating cone (190). In some embodiments, the system (100) includes the urinating cone (190) but no cone storage cone (170) or brush storage cone (180).

In some embodiments, the system (100) includes the cone storage cone (170) and the brush storage cone (180) but no urinating cone (190). In some embodiments, the system (100) includes the cone storage cone (170) and the urinating cone (190) but not brush storage cone (180). In some embodiments, the system (100) includes the brush storage cone (180) and the urinating cone (190) but no cone storage cone (170).

As used herein, the term "about" refers to plus or minus 10% of the referenced number.

The disclosures of the following U.S. Patents are incorporated in their entirety by reference herein: U.S. Pat. No. D 617,895; U.S. Pat. No. D 602,156; U.S. Pat. No. D 414,060; U.S. Patent Pub. No. 2007/0191795; U.S. Pat. No. 6,460,200; U.S. Pat. No. 6,327,716; U.S. Pat. No. 4,612,676; and U.S. Pat. No. 4,282,611.

Various modifications of the invention, in addition to those described herein, will be apparent to those skilled in the art from the foregoing description. Such modifications are also intended to Fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures.

The reference numbers recited in the below claims are solely for ease of examination of this patent application, and are exemplary, and are not intended in any way to limit the scope of the claims to the particular features having the corresponding reference numbers in the drawings.

What is claimed is:

1. A splatter reduction system (100) for reducing splatter on and around a toilet (200) when urinating, wherein the system (100) comprises:
   (a) a weighted base (110) having a base anterior end (112) and a base posterior end (114), wherein the base anterior end (112) comprises a telescopic mounting tube (120) having a tube anterior end (122) and a tube posterior end (124) disposed thereon, wherein the tube posterior end (124) is disposed on the base anterior end (112), wherein the base posterior end (114) comprises a planar terminating end for placing on a ground surface proximal to a toilet (200), wherein the base posterior end (114) comprises a weight component (130) for stability, wherein the base (110) tapers from the terminating base posterior end (114) to the base anterior end (112);
   (b) a segmented horizontal arm assembly (140) comprising a first arm segment (145), a second arm segment (150), and a third arm segment (155), wherein a first arm segment second end (147) is pivotally disposed on the tube anterior end (122), wherein a second arm segment second end (152) is pivotally disposed on a first arm segment first end (146), wherein a third arm segment second end (157) is attachably disposed on a second arm segment first end (151);
   (c) a handle (160) disposed on a terminating third arm segment first end (156);
   (d) a disposable cone storage cone (170) having an open cone storage cone anterior end (172) and a cone storage cone posterior end (174), wherein the cone storage cone (170) is disposed in the first arm segment (145) between the first arm segment first end (146) and the first arm segment second end (147), wherein the cone storage cone (170) tapers from the open cone storage cone anterior end (172) to the cone storage cone posterior end (174), wherein one or more disposable cones (176) are disposed in the cone storage cone (170) via stacking;
   (e) a brush storage cone (180) having an open brush storage cone anterior end (182) and a brush storage cone posterior end (184), wherein the brush storage cone (180) is disposed in the second arm segment (150) between the second arm segment first end (151) and the second arm segment second end (152), wherein the brush storage cone (180) tapers from the brush storage cone anterior end (182) to the brush storage cone posterior end (184), wherein a drain aperture (186) is disposed in the brush storage cone posterior end (184), wherein a cleaning solution is disposed in the brush storage cone (180), wherein a cleaning brush (188) is disposed in the brush storage cone (180) for storage, wherein the cleaning brush (188) is soaked in the cleaning solution;
   (f) a urinating cone (190) having an open urinating cone anterior end (192) and a urinating cone posterior end (194), wherein the urinating cone (190) is disposed in the third arm segment (155) between the third arm segment first end (156) and the third arm segment second end (157), wherein the urinating cone (190) tapers from the urinating cone anterior end (192) to the urinating cone posterior end (194), wherein a urinating aperture (196) is disposed in the urinating cone posterior end (194); and
   (g) the toilet (200) having a toilet bowl (202);
wherein the urinating cone (190) is centrally disposed over the toilet bowl (202) via pivoting the horizontal arm assembly (140), wherein a urinating cone height (198) is adjusted via the telescopic mounting tube (120), wherein a disposable cone (176) is placed in the urinating cone (190) before urinating, then discarded into the toilet bowl (202) upon completion of urination, wherein the cleaning brush (188) is used to clean the urinating cone (190) after urination.

2. The system (100) of claim 1, wherein the urinating cone (190) comprises an adjustable angle on a horizontal axis (210).

3. A splatter reduction system (100) for reducing splatter on and around a toilet (200) when urinating, wherein the system (100) comprises:
   (a) a weighted base (110) having a base anterior end (112) and a base posterior end (114), wherein the base anterior end (112) comprises a telescopic mounting tube (120) having a tube anterior end (122) and a tube posterior end (124) disposed thereon, wherein the tube posterior end (124) is disposed on the base anterior end (112), wherein the base posterior end (114) comprises a planar terminating end for placing on a ground surface proximal to a toilet (200), wherein the base posterior end (114) comprises a weight component (130) for stability, wherein the base (110) tapers from the terminating base posterior end (114) to the base anterior end (112);
   (b) a horizontal arm assembly (140) comprising a first arm segment (145), a second arm segment (150), and a third arm segment (155), wherein a first arm segment second end (147) is pivotally disposed on the tube anterior end (122), wherein a second arm segment second end (152) is contiguous with a first arm segment first end (146), wherein a third arm segment second end (157) is attachably disposed on a second arm segment first end (151);
   (c) a handle (160) disposed on a terminating third arm segment first end (156);
   (d) a disposable cone storage cone (170) having an open cone storage cone anterior end (172) and a cone storage cone posterior end (174), wherein the cone storage cone (170) is disposed in the first arm segment (145) between the first arm segment first end (146) and the first arm segment second end (147), wherein the cone storage cone (170) tapers from the open cone storage cone anterior end (172) to the cone storage cone posterior end (174), wherein one or more disposable cones (176) are disposed in the cone storage cone (170) via stacking;
   (e) a brush storage cone (180) having an open brush storage cone anterior end (182) and a brush storage cone posterior end (184), wherein the brush storage cone (180) is disposed in the second arm segment (150) between the second arm segment first end (151) and the second arm segment second end (152), wherein the brush storage cone (180) tapers from the brush storage cone anterior end (182) to the brush storage cone posterior end (184), wherein a drain aperture (186) is disposed in the brush storage cone posterior end (184), wherein a cleaning solution is disposed in the brush storage cone (180), wherein a cleaning brush (188) is disposed in the brush storage cone (180) for storage, wherein the cleaning brush (188) is soaked in the cleaning solution;
   (f) a urinating cone (190) having an open urinating cone anterior end (192) and a urinating cone posterior end (194), wherein the urinating cone (190) is disposed in the third arm segment (155) between the third arm segment first end (156) and the third arm segment second end (157), wherein the urinating cone (190) tapers from the urinating cone anterior end (192) to the urinating cone posterior end (194), wherein a urinating aperture (196) is disposed in the urinating cone posterior end (194); and (g) the toilet (200) having a toilet bowl (202);

wherein the urinating cone (190) is centrally disposed over the toilet bowl (202) via pivoting the horizontal arm assembly (140), wherein a urinating cone height (198) is adjusted via the telescopic mounting tube (120), wherein a disposable cone (176) is placed in the urinating cone (190) before urinating, then discarded into the toilet bowl (202) upon completion of urination, wherein the cleaning brush (188) is used to clean the urinating cone (190) after urination.

\* \* \* \* \*